(12) United States Patent
Watanabe et al.

(10) Patent No.: US 6,441,218 B2
(45) Date of Patent: Aug. 27, 2002

(54) PROCESS FOR PRODUCING 2-SUBSTITUTED PROPIONIC ACID

(75) Inventors: Saisuke Watanabe, Kawasaki; Kazuharu Suyama, Tokyo, both of (JP)

(73) Assignee: Nippon Petrochemicals Company, Limited, Tokyo (JP)

( * ) Notice: Subject to any disclaimer, the term of this patent is extended or adjusted under 35 U.S.C. 154(b) by 0 days.

(21) Appl. No.: 09/767,669

(22) Filed: Jan. 23, 2001

(30) Foreign Application Priority Data

Feb. 10, 2000 (JP) ........................ 2000-033231
Jun. 21, 2000 (JP) ........................ 2000-185993

(51) Int. Cl.$^7$ .............................................. C07C 69/76
(52) U.S. Cl. ........................... 560/54; 560/51; 562/459
(58) Field of Search .............................. 560/51, 57, 64, 560/76, 97, 54; 562/459

(56) References Cited

U.S. PATENT DOCUMENTS 4,161,538 A * 7/1979 Terada et al. ............... 424/317

5,082,966 A * 1/1992 Moffatt .......................... 560/11

FOREIGN PATENT DOCUMENTS

| JP | 58-4699 | 1/1983 | |
| JP | 62-161740 | 7/1987 | |
| JP | 2000-327603 | * 11/2000 | ........... C07C/27/02 |
| WO | WO97/47581 | 12/1997 | |

OTHER PUBLICATIONS

Yukio Masaki et al, "Unprecedented Polymer–Supported π–Acid: Synthesis and Its Application as a Promoter to the Monothioacetalization of Acetals", Tet. Lett., vol. 39 (1998), pp. 5799–5802.*

* cited by examiner

Primary Examiner—Paul J. Killos
(74) Attorney, Agent, or Firm—Hollander Law Firm, P.L.C.

(57) ABSTRACT

Adipic acid diester is caused to react with alkoxide $M(OR)_n$, wherein R is an alkyl group and M is an alkali metal or alkaline earth metal, the reaction product is successively subjected either to coupling with halomethylstyrene followed by carbonylation, or to coupling with 2-(halomethylphenyl)propionic acid or its ester followed by decarboxylation and hydrolysis. With this process, it is possible to produce more efficiently a specific 2-substituted propionic acid, loxoprofen.

39 Claims, No Drawings

PROCESS FOR PRODUCING 2-SUBSTITUTED PROPIONIC ACID

BACKGROUND OF THE INVENTION

(1) Field of the Invention

The present invention relates to a process for producing 2-substituted propionic acid having effects as anti-inflammatory agent, analgesic, antipyretic and so forth.

(2) Prior Art

As disclosed in Japanese Patent Publication No. S58-004699, compounds of 2-substituted propionic acid have effects as anti-inflammatory agent, analgesic and antipyretic. Especially, 2-[4-(2-oxocyclopentan-1-yl methyl)phenyl] propionic acid, "loxoprofen", is commercially available as an excellent analgesic drug.

In addition to the above disclosure, as disclosed in Japanese Laid-Open Patent Publication No. S62-161740, the conventional preparation process includes the steps of (1) coupling reaction of 2-(p-halomethylphenyl)propionic acid ester with 2-cyclopentanone carboxylic acid ester in the presence of a base, and (2) decarboxylation and hydrolysis of ester with an acid.

In the above first coupling step, the hydrogen atom at α-position of 2-cyclopentanone carboxylic acid ester, is taken off to give 2-(alkoxycarbonyl)-cyclopentenolate anion, which attacks the halomethyl group of 2-(p-halomethylphenyl)propionic acid ester to generate carbon-carbon bond so that the fundamental skeletal structure of loxoprofen is formed.

Although above 2-(p-halomethylphenyl)propionic acid ester is relatively inexpensive, 2-cyclopentanone carboxylic acid ester is an expensive reagent.

Furthermore, the reaction in the presence of a base, the base likely causes side reaction with halomethyl group of 2-(p-halomethylphenyl)propionic acid ester.

Proposed in PCT International Publication No. WO 97/47581 is a method that loxoprofen is produced through carbonylation of p-chloromethylstyrene in the presence of a transition metal complex catalyst. That is, the method comprises (i) carbonylation of p-chloromethylstyrene, (ii) coupling with cyclopentanone carboxylic acid ester, and (iii) decarboxylation and hydrolysis.

The above method of utilizing carbonylation is advantageous in industrial working because the structure of substituted styrene can easily be converted into the structure of substituted propionic acid ester.

However, p-chloromethylstyrene has a high polymerization activity in the presence of heat, light and pressure owing to the existence of substituted chloromethyl groups bonded to the benzene ring. Particularly in the carbonylation with a transition metal complex catalyst, p-chloromethylstyrene is liable to polymerize. This fact may be apprehended in view of the fact that commercially available p-chloromethylstyrene usually contains polymerization inhibitor and that polymerization inhibitor may be added in carbonylation as described on page 6 of the foregoing International Publication.

As described above, p-chloromethylstyrene is liable to cause self-polymerization, so that, according to the above International Publication, polymerization inhibitor is added during the carbonylation as above. In addition, it is required to use solvents as much as several times to several tens times, mostly over ten times the volume of p-chloromethylstyrene as substrate in all the examples on carbonylation.

However, the necessity for large quantity of solvent relative to the substrate substance of p-chloromethylstyrene is not advantageous in industrial practice.

In the method as described in the above International Publication, highly reactive vinyl groups are reacted to convert into other less reactive substituents in the first step among plurality of steps. This method cannot always be regarded as reasonable in industrial scale process in view of the fact that the high reactivity of vinyl group is not taken into consideration sufficiently.

Moreover, the method disclosed in the above International Publication cannot be said as inexpensive because expensive cyclopentanone carboxylic acid alkyl ester is used as a starting material. In addition, the yield is not always satisfactory either.

As mentioned above, the most suitable method for producing loxoprofen has not yet been proposed, and a more efficient method is wanted.

BRIEF SUMMARY OF THE INVENTION

It is the object of the present invention to provide a process for producing loxoprofen using adipic acid diester as one of starting materials, which is more effective as compared with conventional methods.

More particularly, a first aspect of the present invention relates to a process for producing a compound as represented by the following general formula II (hereinafter referred to as "compound II"):

II

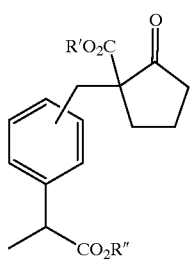

wherein R' represents an alkyl group having 4 or less carbon atoms, R" represents hydrogen atom or an alkyl group having 4 or less carbon atoms, and R' and R" can be either the same or different, which process comprises the steps of:

to cause adipic acid diester to react with alkoxide as represented by the following general formula:

M(OR)$_n$ wherein R represents an alkyl group having 5 or less carbon atoms, M represents alkali metal or alkaline earth metal, n represents the number corresponding to the valence of M and (OR)'s of n in number can be either the same or different, to subject successively the above product to coupling with halomethylstyrene to obtain the compound as represented by the following general formula I (hereinafter referred to as "compound I"):

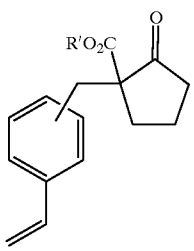

wherein R' represents an alkyl group having 4 or less carbon atoms, and to cause the above compound I to react with carbon monoxide and water or alcohol in the presence of a metal catalyst to obtain the above compound II.

A second aspect of the present invention relates to a process for producing 2-substituted propionic acid as represented by the following general formula III (hereinafter referred to as "compound III"):

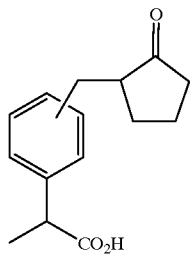

which process comprises the steps of (1-1) to (1-3):

step (1-1) to cause adipic acid diester to react with alkoxide as represented by the following general formula:

M(OR)$_n$ wherein R represents an alkyl group having 5 or less carbon atoms, M represents alkali metal or alkaline earth metal, n represents the number corresponding to the valence of M, and (OR)'s of n in number can be either the same or different, and successively subjecting the above product to coupling with halomethylstyrene to obtain the compound I as represented by the following general formula I:

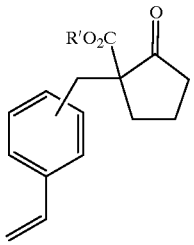

wherein R' represents an alkyl group having 4 or less carbon atoms, step (1-2) to cause the above compound I to react with carbon monoxide and water or alcohol in the presence of metal catalyst to obtain a compound II as represented by the following general formula II:

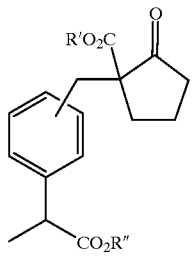

wherein R' represents an alkyl group having 4 or less carbon atoms, R" represents hydrogen atom or an alkyl group having 4 or less carbon atoms, and R' and R" can be either the same or different, and step (1-3) to subject the above compound II to decarboxylation and hydrolysis to obtain the above compound III.

A third aspect of the present invention relates to a process for the production as described in the first or second aspect, wherein halomethylstyrene is chloromethylstyrene.

According to the above methods, the halomethyl group of halomethylstyrene is converted into a particular substituent, so that the liability for self-polymerization of vinyl group is reduced. Therefore, a large quantity of solvent is not required in carbonylation. Furthermore, it is possible to produce 2-substituted propionic acid effectively using an inexpensive starting material.

A fourth aspect of the present invention relates to a process for producing a compound II as represented by the following general formula II:

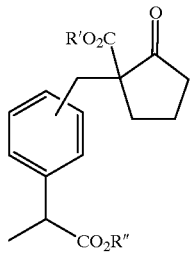

wherein R' represents an alkyl group having 4 or less carbon atoms, R" represents hydrogen atom or an alkyl group having 4 or less carbon atoms, and R' and R" can be either the same or different, which process comprises the steps of:

causing adipic acid diester to react with alkoxide as represented by the following general formula:

M(OR)$_n$ wherein R represents an alkyl group having 5 or less carbon atoms, M represents alkali metal or alkaline earth metal, n represents the number corresponding to the valence of M, and (OR)'s of n in number can be either the same or different, successively subjecting the product obtained above to coupling with a compound as represented by the following general formula IV (hereinafter referred to as "compound IV") to obtain the above compound II,

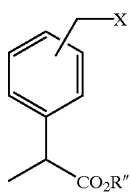

IV wherein X represents halogen atom, and R" represents hydrogen atom or an alkyl group having 4 or less carbon atoms.

A fifth aspect of the present invention relates to a process for producing 2-substituted propionic acid as represented by the following formula III (compound III):

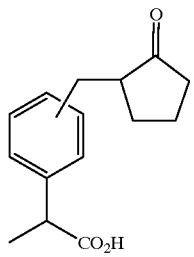

III which process comprises the steps of (2-1) and (2-2):

step (2-1) to cause adipic acid diester to react with alkoxide as represented by the following general formula:

$M(OR)_n$ wherein R represents an alkyl group having 5 or less carbon atoms, M represents alkali metal or alkaline earth metal, n represents the number corresponding to the valence of M, and (OR)'s of n in number can be either the same or different, and successively subjecting the product obtained above to coupling with a compound IV as represented by the following general formula IV to obtain a compound II as represented by the general formula II:

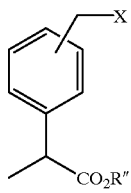

IV wherein X represents halogen atom, and R" represents hydrogen atom or an alkyl group having 4 or less carbon atoms, and

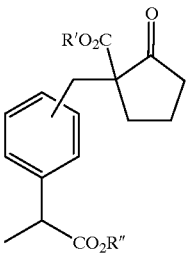

II wherein R' represents an alkyl group having 4 or less carbon atoms, R" represents hydrogen atom or an alkyl group having 4 or less carbon atoms, and R' and R" can be either the same or different, step (2-2) to subject the above compound II to decarboxylation and hydrolysis to obtain the above compound III.

A sixth aspect of the present invention relates to a process for the production as described in the fourth or fifth aspect, wherein halogen atom X in the general formula IV is chlorine or bromine.

A seventh aspect of the present invention relates to a process for the production as described in any one of fourth to sixth aspects, wherein R" in the general formula IV is hydrogen atom, or methyl or ethyl group.

An eighth aspect of the present invention relates to a production process as described in any one of first to seventh aspects, wherein the effective amount of alkoxide, $M(OR)_n$, is 0.7 to 1 equivalent relative to 1 mole of adipic acid diester during the reaction.

A ninth aspect of the present invention relates to a production process as described in any one of first to eighth aspects, wherein adipic acid diester is dimethyl adipate or diethyl adipate.

A tenth aspect of the present invention relates to a production process as described in any of first to ninth aspects, wherein alkoxide, $M(OR)_n$, is sodium methoxide or sodium ethoxide.

DETAILED DESCRIPTION OF THE INVENTION

In all the processes for production according to the present invention, adipic acid diester is used as a starting material. One process comprises the step (1-1): [coupling], step (1-2): [carbonylation] and step (1-3): [decarboxylation and hydrolysis]. The other process comprises the step (2-1): [coupling] and step (2-2) [decarboxylation and hydrolysis].

In the first place, the production process comprising steps of (1-1) to (1-3) will be described in the order of steps.

Step (1-1): [Coupling]

In step (1-1), after Dieckmann condensation of dimethyl adipate with the above alkoxide $M(OR)_n$, is carried out to produce 2-(alkoxycarbonyl)cyclopentenolate anion, the above obtained compound is successively subjected to the coupling with halomethylstyrene to obtain a compound I.

In the present step, 2-(alkoxycarbonyl)cyclopentenolate anion is produced as an intermediate product, which is then subjected to coupling with halomethylstyrene without isolation. Although both the compounds are unsaturated ones, it is advantageous because the carbon-carbon double bonds in halomethylstyrene are almost inactive in this reaction. Because 2-(alkoxycarbonyl)cyclopentenolate anion is not isolated as ester or acid, the operation of reaction is simple and the yield is higher than that in the case with effecting isolation.

Among adipic acid diesters, adipic acid dialkyl esters are preferable. Exemplified as the alkyl groups for the above dialkyl esters are those having 4 or less carbon atoms such as Me (methyl), Et (ethyl), n-Pr (propyl), iso-Pr, n-Bu (butyl), iso-Bu, sec-Bu and tert-Bu. Two alkyl groups contained in the adipic acid dialkyl ester can be either the same or different. They have preferably the same alkyl groups of Me, Et, n-Pr or iso-Bu, more preferably they are dimethyl adipate and diethyl adipate.

As the alkoxide, $M(OR)_n$, commercially available common ones can be used. The alkali metals and alkaline earth metals of "M" are exemplified by sodium, potassium, lithium, calcium and magnesium. Exemplified as "R" are alkyl groups having 5 or less carbon atoms such as Me, Et, n-Pr, iso-Pr, n-Bu, iso-Bu, sec-Bu, tert-Bu, 1-pentyl, 2-pentyl, 3-pentyl, neopentyl and tert-amyl. The symbol "n" represents the number corresponding to the valence of M, and (OR)'s of n in number can be either the same or different. Preferably, it has the same alkoxyl groups, wherein R is an alkyl group such as Me, Et, n-Pr or iso-Pr.

Exemplified as the foregoing alkoxides are lithium methoxide, sodium methoxide, potassium methoxide, calcium methoxide and magnesium methoxide; lithium ethoxide, sodium ethoxide, potassium ethoxide, calcium ethoxide and magnesium ethoxide; lithium n-propoxide, sodium n-propoxide, potassium n-propoxide, calcium n-propoxide and magnesium n-propoxide; lithium iso-propoxide, sodium iso-propoxide, potassium iso-propoxide, calcium iso-propoxide and magnesium iso-propoxide; lithium n-butoxide, sodium n-butoxide, potassium n-butoxide, calcium n-butoxide and magnesium n-butoxide; lithium iso-butoxide, sodium iso-butoxide, potassium iso-butoxide, calcium iso-butoxide and magnesium iso-butoxide; lithium sec-butoxide, sodium sec-butoxide, potassium sec-butoxide, calcium sec-butoxide and magnesium sec-butoxide; lithium tert-butoxide, sodium tert-butoxide, potassium tert-butoxide, calcium tert-butoxide and magnesium tert-butoxide; lithium 1-pentoxide, sodium 1-pentoxide, potassium 1-pentoxide, calcium 1-pentoxide and magnesium 1-pentoxide; lithium 2-pentoxide, sodium 2-pentoxide, potassium 2-pentoxide, calcium 2-pentoxide and magnesium 2-pentoxide; lithium 3-pentoxide sodium 3-pentoxide, potassium 3-pentoxide, calcium 3-pentoxide and magnesium 3-pentoxide; lithium tert-amyloxide, sodium tert-amyloxide, potassium tert-amyloxide, calcium tert-amyloxide and magnesium tert-amyloxide; lithium neopentoxide, sodium neopentoxide, potassium neopentoxide, calcium neopentoxide and magnesium neopentoxide; and so forth. Exemplified as particularly suitable ones are lithium methoxide, sodium methoxide and potassium methoxide, lithium ethoxide, sodium ethoxide and potassium ethoxide, lithium iso-propoxide, sodium iso-propoxide and potassium iso-propoxide, and lithium tert-butoxide, sodium tert-butoxide and potassium tert-butoxide.

As for the halomethylstyrene, styrene having fluoromethyl-, chloromethyl-, bromomethyl- or iodomethyl group is used. Preferable ones are chloromethylstyrene and bromomethylstyrene. Among them, chloromethylstyrene is desirable, particularly p-chloromethylstyrene is preferable.

In the present step, reaction solvents are preferably used. The solvents can vary depending on the kinds of adipic acid diesters.

In the initial condensation reaction of adipic acid diester with alkoxide, 1 equivalent of alcohol is produced as a by-product. By means of continuous or intermittent removal of the alcohol, the reaction proceeds to produce the above-mentioned 2-(alkoxycarbonyl)cyclopentenolate anion.

Therefore, the procedure for removing selectively the produced alcohol from the reaction system is inevitable for the purpose of acceleration of reaction. As the removal operation, it is convenient to distill off with heating under atmospheric pressure or reduced pressure. Therefore, when a solvent is used for the reaction, its boiling point must be the same as or higher than that of the by-product alcohol.

For example, when dimethyl adipate is used as adipic acid diester, a solvent having a boiling point higher than that of methanol (about 65° C.) is used. The solvents are exemplified by nitrogen-containing compounds such as dimethyl formamide and acetonitrile; ether such as tetrahydrofuran; ketones such as acetone and methyl ethyl ketone; ester such as ethyl acetate; aromatic hydrocarbons such as benzene, toluene and xylene; aliphatic hydrocarbons such as octane, nonane, decane and isododecane; and the mixed solvents of them. Among them, toluene and benzene are preferable, and toluene is more preferable.

When adipic acid diester other than dimethyl adipate is used, solvents conforming to the above description can be used.

Concerning the use quantity of solvent for reaction, for example, 500 to 5,000 ml of solvent is used relative to 1 mole of adipic acid diester. The amount is preferably 800 to 3,000 ml, particularly 1,000 to 2,000 ml.

The above $M(OR)_n$ and adipic acid diester are allowed to react together, preferably in a solvent, in a temperature range of 0 to 300° C., preferably 10 to 250° C., more preferably 20 to 200° C., within 24 hours, preferably for 6 hours, and more preferably for one hour.

During the reaction, the produced alcohol is distilled off under atmospheric pressure or reduced pressure. In order to remove the alcohol completely, it is preferable to remove simultaneously a part of solvent. In the case when a reaction solvent is distilled off, the solvent can be newly supplemented.

When alkoxide is reacted with adipic acid ester, the alkoxide can be used in the form of solid, for example, it is dried and preferably as fine powder, or as a solution of alkoxide in alcohol. Preferably, alcoholic solution containing dissolved alkoxide is used. The alcohol content is distilled off before the reaction with adipic acid ester starts substantially. By carrying out this procedure, suspension containing alkoxide finely dispersed in a reaction mixture is obtained, which can produce a desirable result.

As to the amount of alkoxide, for example, 0.1 to 10 equivalents of alkoxide can be used for 1 mole of adipic acid diester. When M is an alkali metal, 1 mole of alkoxide corresponds to 1 equivalent, and when M is an alkaline earth metal, 1 mole of alkoxide corresponds to 2 equivalents. It is preferable that 0.5 to 2 equivalents of alkoxide is used relative to 1 mole of adipic acid diester. It is particularly desirable that the effective amount of alkoxide is 0.7 to 1 equivalent during reaction.

When alcohol remains after the reaction, the alcohol can be distilled off.

By the above reaction of adipic acid diester with alkoxide, the above 2-(alkoxycarbonyl)cyclopentenolate anion can be obtained, the latter of which is successively subjected to coupling with halomethylstyrene without isolation. Although the by-product alcohol is distilled off in order to accelerate reaction as described above, it is not always necessary that the reaction mixture is completely free from the by-product alcohol. The reaction mixture containing a certain amount of alcohol as by-product can be fed into the next step of coupling reaction without any treatment. If unreacted substances coexist, it is rather favorable for the next coupling reaction. Therefore, the reaction mixture containing unreacted substances can be fed directly to the next coupling reaction.

Thus, halomethylstyrene is added to the obtained reaction mixture to carry out coupling reaction. The amount of halomethylstyrene is 0.1 to 20 moles, preferably 0.5 to 2 moles, more preferably 0.7 to 1.5 moles, relative to 1 mole of previously added adipic acid diester.

The temperature of reaction is in the range of 0 to 150° C., preferably 20 to 150° C., more preferably room temperature to 80° C.

The time length of reaction is 24 hours or less, preferably 0.1 to 20 hours, more preferably 1 to 10 hours.

Though the coupling reaction can be carried without reaction solvent, it is also possible to use a solvent. In the like manner as the foregoing, usable solvents are exemplified by nitrogen-containing compounds such as dimethyl formamide and acetonitrile; ether such as tetrahydrofuran; acetals; ketones such as acetone and methyl ethyl ketone; ester such as ethyl acetate; aromatic hydrocarbons such as benzene, toluene and xylene; aliphatic hydrocarbons such as octane, nonane, decane and isododecane; and the mixed solvents of them. Among them, toluene and benzene are preferable, and toluene is more preferable.

As to the amount of reaction solvents, for example, 500 to 5,000 ml, preferably 800 to 3,000 ml, more preferably 1,000 to 2,000 ml, can be used relative to 1 mole of adipic acid diester that is added previously.

After the reaction, residual base is neutralized with acid, which is followed by extraction and water washing, and then extraction solvent is removed. When the reaction solvent is water soluble one, it is removed under reduced pressure. After that, an extraction solvent is added and extraction and water washing are carried out, and further, the extraction solvent is removed. As the extraction solvents, appropriate ones can be used, while toluene is usually employed. It is not always necessary to remove completely the extraction solvents remaining after extraction, as long as they do not have influence on the next step. They can be used as dilution solvents in the next step (1-2).

Compound I can be obtained according to the above method, and it is used in the next step (1-2). Compound I can be supplied to step (1-2) after refined further by methods of distillation or others, but additional refining is not necessary.

In the obtained product, the compound as represented by the formula V (hereinafter referred to as "compound V") is sometimes present in a small amount. However, it is converted finally into the intended compound III, therefore its mixing does not cause any trouble.

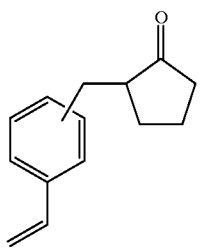

V

Halomethylstyrene used in step (1-1) is liable to polymerize by itself. The polymerization is further accelerated particularly when it is handled in a heated and pressurized system. Therefore, when halomethylstyrene is directly subjected to carbonylation, it is necessary to dilute the reaction system with a large amount of solvent as mentioned above, which is industrially costly. However, a compound I, which is obtained by coupling halomethylstyrene with cyclopentanone carboxylic acid ester, is difficult to polymerize by itself. As shown by the examples of the present invention, the dilution solvent required in carbonylation of compound I is only several times or less the amount of substrate.

Further, in the method of the present invention, the amount of by-product resulting from the polymerization of halomethylstyrene is small, which is favorable also from the viewpoint of waste disposal. Accordingly, the present invention is superior by far in efficiency to the conventional method comprising (i) carbonylation of p-chloromethylstyrene, (ii) coupling with cyclopentanone carboxylic acid ester, and (iii) decarboxylation and hydrolysis. Step (1-2): [Carbonylation]

In the present step (1-2), the compound I resulting from the above step (1-1) is caused to react with carbon monoxide and water or alcohol, in the presence of catalyst and dilution solvents, or with addition of polymerization inhibitor if necessary, to obtain a compound II. The catalysts used in the present step is any selected from the group of (i) metal complex itself, (ii) substance comprising metal complex and ligand, and (iii) substance comprising metal complex, ligand and additive.

When a catalyst corresponding to (ii) or (iii) is used, it is desirable to use the procedure for developing catalyst activity by mixing metal complex, or metal complex and additive, with alcohol to be used in the reaction, then adding ligand.

As metal complexes, transition metal complexes, preferably complexes of transition metal of group VIII, more preferably those of cobalt, rhodium, platinum and palladium can be used. As the examples, there are $Co_2(CO)_8$, $RhCl(PPh_3)_3$, wherein "Ph" represents phenyl group, $RhCl(CO)(PPh_3)_2$, $H_2PtCl_6$, Pd carbon, Pd black, $Pd(PPh_3)_4$, $Pd(PPhBu_2)_2$, $Pd(P Bu_3)_2$, $Pd(P(OPh)_3)_4$, $Pd(P(OEt)_3)_4$, $Pd(C_2H_4)(PPh_3)_2$, $Pd(PhCN)_2(BF_4)_2$, $Pd(MeCN)_4(BF_4)_2$, $Pd(PhCN)_2(PPh_3)_2(BF_4)_2$, $Pd(MeCN)_2(PPh_3)_2(BF_4)_2$, $Pd(acac)_2$, wherein "acac" represents acetylacetonato group, $Pd_2(dba)_3CHCl_3$, $Pd(dba)_2$, wherein "dba" represents dibenzylideneacetone, PdO, PdS, $Pd(NO_3)_2$, $PdSO_4$, $PdX_2$, wherein "X" represents Cl, Br, I, $OCOCF_3$ or OCOMe, $PdX_2(PhCN)_2$, $PdX_2(MeCN)_2$, $PdX_2(CO)_2$, wherein "X" represents Cl, Br, or I, $Pd(COD)_2$, $PdX_2(COD)_2$, wherein "X" represents Cl, Br or I and "COD" represents 1,5-cyclooctadiene, $Pd(MA)(PPh_3)_2$, wherein "MA" represents maleic anhydride, $M_2PdX_4$, wherein "X" represents Cl, Br, I or OCOMe and "M" represents H, $NH_4$, Li, Na or K, $PdX_2(PArAr'Ar")_2$, wherein "X" represents Cl, Br or I and Ar, Ar' or Ar" represents the same or different aryl group, $PdX_2(PPh_3)_2$, $PdX_2(PRPh_2)_2$, $PdX_2(PR_2Ph)_2$, $PdX_2(PR_3)_2$, $Pd_2X_4(PR_3)_2$, wherein "X" represents Cl, Br or I and "R" represents Me, Et, Pr, Bu, OPh, menthyl group or cyclohexyl group, $PdX_2(dppf)$, wherein "X" represents Cl, Br or I and "dppf" represents bis(diphenylphosphino)ferrocene, $PdX_2(Ph_2P(CH_2)_nPPh_2)$, wherein "X" represents Cl, Br or I and "n" represents an integer from 1 to 4, $PdR_2(PR'_3)_2$, wherein R and R' represents Me, Et, Pr, Bu, OPh or Ph, $PdXR(PR'_3)_2$, wherein "X" represents Cl, Br or I, "R" represents H, Me, Et, Pr, Bu, Ph, $CH_2Ph$ or COMe and R' represents Me, Et, Pr, Bu, OPh, Ph or cyclohexyl group, $[Pd(\eta^3\text{-}CH_2CHCH_2)X]_2$, $[Pd(\eta^3\text{-}CH_2CHCH_2)X(PPh_3)]$, $[Pd(\eta^3\text{-}CH_2CHCHCH_2X)X]_2$, wherein "X" represents Cl, Br or I, $Pd(\eta^3\text{-}CH_2CHCH_2)_2$, $Pd(\eta^3\text{-}CH_2CHCH_2)(\eta^5\text{-}C_5H_5)$ and so forth, but the metal complexes used in the present step are not limited to these.

The amounts of metal complex is 1 mole or less relative to 1 mole of compound I, preferably in the range of 0.00001 to 0.1 mole, more preferably 0.0001 to 0.01 mole.

Ligands are compounds that have the property to produce coordination compounds, and phosphines or phosphites are favorably used, and more favorably triarylphosphines. As the examples, there are $PPh_3$, $PArAr'Ar''$ (Ar, Ar' and Ar'' are the same or different aryl groups), $PRPh_2$, $PR_2Ph$, $PR_3$, wherein "R" represents Me, Et, n-Pr, iso-Pr, n-Bu, menthyl group or cyclohexyl group, $Ph_2P(CH_2)_nPPh_2$, wherein "n" represents an integer from 1 to 4, bis(diphenylphosphino)ferrocene, $P(OPh)_3$ and so forth, but the ligands used in the present step are not limited to these.

The amount of ligand is 10 equivalent or less relative to 1 equivalent of metal complex, preferably 5 equivalent or less, more preferably 2 to 4 equivalent.

As additives, inorganic substances are used, preferably tin chloride, copper oxide, and alkali metal salts or alkaline earth metal salts. Among them, alkali metal salts are favorable. As the examples, there are $SnCl_2$, $CuCl_2$, $MgCl_2$, $CaCl_2$, NaCl, NaBr, LiCl, LiBr, KCl, KBr and so forth, but the additives used in the present step are not limited to these.

The additive can be Brønsted acid and Lewis acid depending on the metal complexes to be used. As Brønsted acids, it is preferable to use the ones, which counter anions coordinate weakly or do not coordinate at all with metal atoms. As the examples, there are p-toluenesulfonic acid, trifluoromethanesulfonic acid, trifluoroacetic acid, $HBF_4$, $HBAr_4$, wherein "Ar" represents aryl group, $HPF_6$ and so forth, but Brønsted acids used in the present step are not limited to these. From the viewpoint of easy handling, p-toluenesulfonic acid is particularly favorable.

As Lewis acids, general compounds can be used, preferably those comprising B, Al, Ti, Zn, Sn, Sb and so forth. Among them, those comprising B, Al or Ti are favorable. As substances to be connected with these elements, there are alkoxyl group, halogen atom, oxygen atom, hydrogen atom and so forth. Among theme, halogen is favorable. As the examples of Lewis acids, there are $TiX_4$, $BX_3$, $AlX_3$, $ZnX_2$, $SnX_4$, $SbX_5$, wherein "X" represents halogen atom, $Ti(OR)_nX_{4-n}$, wherein "R" represents methyl group, ethyl group, isopropyl group or butyl group, "X" represents halogen atom, and "n" represents an integer from 1 to 4, $TiH_nCl_{4-n}$, wherein "n" represents an integer from 1 to 3, $Al(OR)_3$, $Zn(OR)_2$, wherein "R" represents methyl group, ethyl group or isopropyl group, $TiO_2$, $Al_2O_3$, $ZnO_2$, $SnO_2$, $SbO_5$ and so forth, but Lewis acids used in the present step are not limited to these.

These Lewis acids in themselves are difficult to handle. Therefore, it is preferable to use them in the form of complexes containing water, ether, alcohol, ester, carboxylic acid or THF (tetrahydrofuran) as ligand. As the examples, there are $BF_3$—$OEt_2$, $BF_3$—$OH_2$, $BF_3$—$(THF)_2$, $TiCl_4$—$(THF)_2$, $AlCl_3$—$(H_2O)_n$ and so forth.

The amount of additive is 20 equivalents or less relative to 1 equivalent of metal complex, preferably 0.1 to 10 equivalents, more preferably 1 to 4 equivalents.

As dilution solvents, commonly available organic solvents can be used. As the examples, there are benzene, toluene, xylene, tetrahydrofuran, acetone, methyl ethyl ketone, ethyl acetate and so forth, but the dilution solvents used in the present step are not limited to these.

As to the amount of dilution solvent, solvent is 20 times or less the volume of compound I, preferably 10 times or less, more preferably 0.5 to 3 times.

As polymerization inhibitors, it is possible to use the compounds that do not hinder carbonylation and reactions thereafter. As the examples, there are nitromethane, nitrobenzene, hydroquinone, $CuCl_2$, $FeCl_2$, 4-tert-butylcatechol, nitrophenol, nitrocresol, 2,6-di-tert-butyl-4-methylphenol, 4-methoxyphenol and so forth, but the polymerization inhibitors used in the present step are not limited particularly. Any mixture comprising two or more kinds of polymerization inhibitors may be used.

The amount of polymerization inhibitor is 10% or less relative to the mass of compound I, preferably 1% or less, more preferably 0.1% or less.

As carbon monoxide, the one having the purity of 20% or more, preferably 50% or more, more preferably 80% or more is used.

Carbon monoxide is prepared in such an amount that 1 mole or more can be supplied to 1 mole of compound I. When hydrogen is present together with carbon monoxide, the partial pressure of carbon monoxide is reduced depending on the amount of coexisting hydrogen. That affects the reaction of the present step somewhat, but the reaction proceeds without any trouble.

Exemplified as alcohols are methyl alcohol, ethyl alcohol, n-propyl alcohol, iso-propyl alcohol, n-butyl alcohol, sec-butyl alcohol, tert-butyl alcohol and iso-butyl alcohol. Methyl alcohol, ethyl alcohol, n-propyl alcohol and iso-propyl alcohol are preferably used, and particularly methyl alcohol and ethyl alcohol are favorable.

The amount of alcohol is 1 mole or more relative to 1 mole of compound I, preferably 1 to 30 moles, more preferably 1 to 3 moles.

An autoclave is charged with the above catalyst, a compound I, water or alcohol, and dilution solvent. Then, at the reaction temperature of 40 to 200° C., preferably 50 to 140° C., more preferably 70 to 100° C., carbon monoxide is pressurized to 0.1 to 30 MPa, preferably 0.2 to 10 MPa, more preferably 2.5 to 7 MPa, and stirring is carried out for 0.1 to 100 hours, preferably 6 to 30 hours, more preferably 8 to 24 hours.

Otherwise, it is also possible to mix catalyst, alcohol and dilution solvent in an autoclave, and then add a compound I successively into the reaction system under the above conditions. In this case, it is preferable to supply a compound I over 0.1 to 100 hours, preferably for 5 to 20 hours, more preferably for 7 to 20 hours.

After the reaction is over, carbon monoxide is removed and the condition is set at normal temperature and pressure. When catalysts are precipitated in a reaction mixture, they can be recovered by filtration and reused. After appropriate filtration of catalysts, separation by distillation can be carried out under reduced pressure to obtain a compound II in high purity. The meta-isomer and para-isomer of compound II have different boiling points, therefore it is possible to separate the mixture of them by rectification. By this method, the pare-isomer can be obtained as a precursor of loxoprofen in high purity.

In the carbonylation carried out in the present step, the temperature is relatively high, and moreover metal catalysts are present. However, a specific substituent group is substituted for halomethyl group of halomethylstyrene such as chloromethyl group of chloromethylstyrene, therefore the polymerization activity of vinyl group is suppressed, so that the reaction of high efficiency can be accomplished.

In the present carbonylation, the compound as represented by the general formula VI (hereinafter referred to as "compound VI") is produced as an isomer of compound II in a small amount,

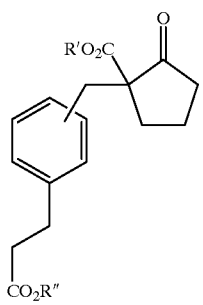

VI wherein R' represents an alkyl group having 4 or less carbon atoms, and R" represents hydrogen atom or an alkyl group having 4 or less carbon atoms.

Further, the compound as represented by the general formula VII resulting from carbonylation of compound V is produced in a trace,

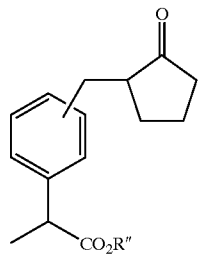

VII wherein R" represents hydrogen atom or an alkyl group having 4 or less carbon atoms.

However, they are converted finally into the intended compound III, therefore their mixing does not cause any trouble. Step (1-3): [Decarboxylation and Hydrolysis]

In the present step, for example, according to the method of the above International Publication, hydrolysis and decarboxylation are carried out using acids such as sulfuric acid and hydrochloric acid.

Otherwise, it is possible to obtain a compound III by heating the compound II obtained in the above step (1-2) together with water and acid in the presence of solvent so as to carry out decarboxylation and hydrolysis step by step. In the present step of decarboxylation and hydrolysis, although the compound II has two ester groups, both groups can be treated at the same time, which is advantageous. The ester group of compound I can be subjected to decarboxylation and hydrolysis before carbonylation of the step (1-2). However, with the hydrolysis and decarboxylation according to the present step, it is possible to treat two ester groups at the same time, even if a compound has two ester groups like compound II.

As acids, commonly available mineral acids can be used. As the examples, there are hydrochloric acid, hydrobromic acid, sulfuric acid, nitric acid and so forth, but the acids used in the present step are not limited to these.

The amount of acids is 20 times or less the mass of compound II, preferably 0.001 to 10 times, more preferably 0.001 to 5 times.

As solvents, hydrophilic organic solvents are preferable. When the reaction is carried out in the presence of hydrophilic organic solvent, the time of reaction can be shortened preferably. Exemplified as hydrophilic organic solvents are tetrahydrofuran, ethyl acetate, acetonitrile, acetic acid and so forth, but the solvents used in the present step are not limited to these. Acetic acid is particularly favorable.

Hydrophilic organic solvents are used in the amount of 20 times or less the mass of compound II, preferably 0.5 to 10 times, more preferably 1 to 5 times.

A reaction vessel is charged with the above acid, solvent and a compound II. Then, at room temperature to 150° C., preferably 50° C. to 120° C., more preferably 90° C. to 110° C., stirring is carried out for 1 to 100 hours, preferably 2 to 24 hours, more preferably 6 to 12 hours. The time of reaction is shortened by removing alcohol produced as by-product from the reaction zone with Dean-Stark apparatus or the like.

After the reaction, extraction is carried out with a hydrophilic organic solvent such as toluene and the solvent is removed to obtain a raw product of compound III. Further, recrystallization can be carried out using good solvent such as ether and bad solvent such as hexane to obtain a compound III in high purity.

In the following, the process for production comprising the steps (2-1) and (2-2) will be described in serial order of the steps.

Step (2-1): [Coupling]

In step (2-1), after the reaction of dimethyl adipate with the above alkoxide $M(OR)_n$ is carried out to produce 2-(alkoxycarbonyl)cyclopentenolate anion, the obtained product is successively subjected to coupling with a compound IV to obtain a compound II.

In the present step, 2-(alkoxycarbonyl)cyclopentenolate anion obtained as an intermediate product, its ester, the corresponding acid and the like, without isolation, can be successively subjected to reaction with a compound IV. Therefore, the operation of reaction is simple, and the yield is higher than in the case with isolation.

As above, it is important to cause 2-(alkoxycarbonyl) cyclopentenolate anion to react with a compound IV without isolation. As long as isolation is excluded, the other simple refining is allowed. In the reaction of alkoxide $M(OR)_n$, as base and adipic acid diester, if only excess of base is avoided, there is no need for apprehension that the base might react with a compound IV as a side reaction.

Adipic acid diester and alkoxide $M(OR)_n$ used in step (2-1) are the same as those described in the above-mentioned step (1-1).

Exemplified as compound IV of 2-(halomethylphenyl) propionic acids or their esters are 2-(fluoromethylphenyl) propionic acid or its ester, 2-(chloromethylphenyl)propionic acid or its ester, 2-(bromomethylphenyl)propionic acid or its ester, and 2-(iodomethylphenyl)propionic acid or its ester. Preferable ones are 2-(chloromethylphenyl)propionic acid, methyl 2-(chloromethylphenyl)propionate, ethyl 2-(chloromethylphenyl)propionate, 2-(bromomethylphenyl) propionic acid, methyl 2-(bromomethylphenyl)propionate and ethyl 2-(bromomethylphenyl)propionate. Among them, methyl 2-(chloromethylphenyl)propionate, ethyl 2-(chloromethylphenyl)propionate, methyl 2-(bromomethylphenyl)propionate and ethyl 2-(bromomethylphenyl)propionate are favorable. Further, methyl 2-(p-chloromethylphenyl)propionate, ethyl 2-(p-chloromethylphenyl)propionate, methyl 2-(p-bromomethylphenyl)propionate and ethyl 2-(p-bromomethylphenyl)propionate are particularly favorable. These acids and esters, especially acids are commercially available at a low price.

When 2-(halomethylphenyl)propionic acid is caused to react with lower alcohol using acid catalyst, it can be easily converted into 2-(halomethylphenyl)propionic acid ester. Accordingly, raw products of the above reaction containing these esters can be used for coupling advantageously.

In the present step, reaction solvents are used preferably. The kinds and the amount of solvent in the condensation reaction of adipic acid diester and alkoxide are the same as those in the above step (1-1).

Further, various conditions in the reaction of adipic acid diester and alkoxide are also the same as those in the above step (1-1). When alcohol remains after the reaction, the alcohol can be distilled off later.

By the above reaction of adipic acid diester with alkoxide, the above 2-(alkoxycarbonyl)cyclopentenolate anion can be obtained, the latter of which is successively subjected to coupling with a compound IV without isolation.

In this case, the by-product of alcohol is distilled off from the viewpoint of accelerating reaction as above-mentioned. However, the reaction mixture does not need to be completely free from by-product of alcohol. The reaction mixture containing a certain amount of alcohol as by-product can be fed into the next step of coupling reaction without any treatment. The reaction mixture containing unreacted substances can also be fed directly to the coupling reaction.

Thus, a compound IV is added to the obtained reaction mixture to carry out coupling reaction. The amount of compound IV is 0.1 to 20 moles relative to 1 mole of adipic acid diester added previously, preferably 0.5 to 2 moles, more preferably 0.7 to 1.5 moles.

The temperature of reaction is in the range of 0 to 150° C., preferably 20 to 150° C., more preferably room temperature to 80° C.

The time of reaction is 24 hours or less, preferably 0.1 to 20 hours, more preferably 1 to 10 hours.

Although coupling reaction can be carried out without reaction solvent, solvents may be used. As to the solvents, the kinds and the amount can be determined in the same way as in the case of the coupling reaction of the above step (1-1).

After the reaction, residual base is neutralized with acid, extraction and water washing are carried out, and then extraction solvent is removed. When reaction solvent is water soluble, the solvent is removed under reduced pressure. Then, extraction solvent is added, extraction and water washing are carried out, and extraction solvent is removed. It is not necessary to remove completely the extraction solvents remaining after extraction, as long as they do not influence the next step.

Compound II can be obtained according to the above method, and it is used in the next step (2-2). Compound II can be refined further by methods such as distillation and then supplied to step (2-2), but the additional refining is not necessary.

In the obtained product, the compound as represented by the formula VII is sometimes present in a trace. However, it is converted finally into the intended compound III, therefore its mixing does not cause any trouble.

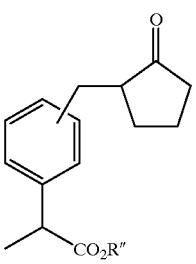

VII wherein
R" is hydrogen atom or an alkyl group having 4 or less carbon atoms, Step (2-2): [Carbonylation and Hydrolysis]

The present step can be carried out in the same way as the above-mentioned step (1-3). That is, acid catalysts, solvents and reaction conditions are all the same as those of the above.

EXAMPLE

In the following, the present invention will be described in more detail referring to examples.

Example 1

[Step (1-1)]

Into a reaction vessel of 15 liters were put 7.2 liters of toluene, 243 g (4.27 mol) of sodium methoxide (purity 95%) and 900 g (5.11 mol) of dimethyl adipate (purity 99%), and the mixture was heated with stirring. After the temperature in the vessel reached 60° C., removal of the solvent of toluene was started under reduced pressure (9.3 kPa (70 mmHg) or less). At the same time, a by-product of methanol was also distilled off. The reaction was carried out for 40 minutes. As the result of measurement after the reaction, the total volume of mixed solvents of toluene and methanol was 6 liters. After that, 5.5 liters of acetone was added to the mixture. Further, 612 g (3.81 mol) of chloromethylstyrene (purity 95%; containing 500 ppm of nitrocresol, nitrophenol and 4-tert-butylcatechol in total; para-isomer: meta-isomer ratio=96:4) was added at room temperature, then the mixture was heated with refluxing for 8 hours.

At the temperature of 60° C. in the vessel, acetone started to be distilled off under reduced pressure. In the middle of that, 2.5 liters of toluene was added. Distilled acetone amounted to 5.5 liters in total.

To the reaction mixture was added 2.7 liters of water and 100 ml of concentrated hydrochloric acid, and extraction was conducted by separation of liquids. Then, the organic phase was washed twice with 1.8 liters of water.

With the removal of toluene under reduced pressure, 1,857.3 g of a liquid in pale yellow was obtained. The purity by gas chromatography of compound I (R' in the general formula I=methyl group (Me)) was 50.3% (para-isomer:meta-isomer ratio=96:4, toluene 40.6%).

Then, 100 mg of the obtained oily substance was treated with thin layer chromatography (developing solvent: ethyl acetate/hexane=30/70, Rf=0.75) to isolate 70 mg of para-isomer of compound I (R'=Me) as a colorless, oily substance. The structure was confirmed with the following spectroscopic data and mass spectrum:

$^1$H NMR (CDCl$_3$, 400 MHz): δ 1.62 (m, 1H), 1.82–2.10 (m, 3H), 2.33–45 (m, 2H), 3.10 (d, J=13.7 Hz, 1H), 3.19 (d, J=13.7 Hz, 1H), 3.72 (s, 3H), 5.22 (dd, J=10.8, 1.0 Hz, 1H), 5.71 (dd, J=17.6, 1.0 Hz, 1H), 6.67 (dd, J=17.6, 10.8 Hz, 1H), 7.08 (d, J=8.3 Hz, 2H), 7.30 (d, J=8.3 Hz, 2H).

$^{13}$C NMR (CDCl$_3$, 100 MHz): δ 19.47, 31.69, 38.36, 38.85, 52.64, 61.48, 13.68, 126.23, 130.33, 136.17, 136.22, 136.67, 171.34, 214.74.

Mass spectrum: 258 (M$^+$), 199, 198, 141, 128, 117 (100%), 115, 104, 91.

[Step (1-2)]

In an autoclave of 5 liters, 1.28 g (7.2 mmol) of PdCl$_2$ and 0.89 g (15.2 mmol) of NaCl were dissolved in 93.0 g (2.90 mol) of methanol, and 3.99 g (15.2 mmol) of PPh$_3$ dissolved in 120 g of toluene was added to the solution. To this mixture were added 186.0 g (5.81 mol) of methanol and 310 g of toluene. Then, 1,857 g of the solution of compound I (R'=Me) synthesized in step (1-1) was added successively with a pump over 18 hours at 90° C. under the pressure of 4.0 MPa of carbon monoxide, and further, reaction was carried out for 3 hours. The above solution of compound I had the purity of 50.3%, substantially 3.62 moles of compound I (R'=Me) and para-isomer:meta-isomer ratio of 96:4, and had 1,000 ppm of 4-tert-butylcatechol added.

After the reaction, the reaction product was analyzed with gas chromatography and gel permeation chromatography. As a result, the conversion was 99.9% and the formation ratio of para-isomer of compound II (R'=R"=Me) and para-isomer of compound VI (R'=R"=Me) was 95:5.

The obtained mixture was subjected to vacuum flash distillation to obtain 460.3 g of a liquid having the melting point of 224° C. (533 Pa (4 mmHg)). The purity of compound II (R'=R"=Me) was 75.6% (para-isomer:meta-isomer ratio=96:4) by means of gas chromatography.

[Step (1-3)]

In this step, 100.0 g of the compound II (R'=R"=Me) obtained in step (1-2) was subjected to refluxing for 5 hours in a solution containing 144 ml of acetic acid/96 ml of 25% aqueous sulfuric acid. In the middle of the reaction, 72 ml of 33% aqueous solution of acetic acid was added. The solvent was distilled off under normal pressure to remove 190 ml of the solvent in total. The contents were cooled, extracted with a solution containing 280 ml of toluene/300 ml of water, and washed thrice with 100 ml of water each time. The solvent was distilled off under reduced pressure to obtain a yellow, oily substance.

The oily substance was recrystallized twice with a mixed solvent of ethyl acetate/hexane to obtain 36.5 g of white, crystalline loxoprofen. The purity by liquid chromatography was 99.9%. The NMR data and the retention time of liquid chromatography coincided completely with those of specimen.

Example 2

[Step (2-1)]

Into a reaction vessel of 300 ml were put 65 ml of toluene, 2.2 g (0.039 mol) of sodium methoxide (purity 95%) and 8.0 g (0.046 mol) of dimethyl adipate (purity 95%), and the mixture was heated with stirring, then the solvent was removed under reduced pressure. After that, 50 ml of acetone was added, then 30 ml of a toluene solution of methyl 2-(bromomethylphenyl)propionate (purity 92.7%; prepared from 9.09 g of 2-(bromomethylphenyl)propionic acid (purity 99.25%) was added at room temperature, and the mixture was heated with refluxing for 4 hours.

Acetone was distilled off under reduced pressure, then 50 ml of toluene, 30 ml of water and 1 ml of concentrated hydrochloric acid were added, and extraction was conducted by separation of liquids. After the organic phase was washed twice with 30 ml of water, filtration was carried out. With the removal of toluene under reduced pressure, 12.9 g of compound II (R'=R"=Me) in pale yellow was obtained as a raw product.

[Step (2-2)]

A solution containing 12 ml of acetic acid/18 ml of 25% aqueous sulfuric acid was added to 12.9 g of compound II (R'=R"=Me) obtained in step (2-1), and refluxing was conducted for 5 hours. The solvent was distilled off under normal pressure, in the middle of which 9 ml of 33% aqueous solution of acetic acid was added. After the distilled solvent amounted to 19 ml, extraction was carried out by separation with 50 ml of toluene and 30 ml of water, and the organic phase was washed with 50 ml of water. With the removal of the solvent under reduced pressure, 8.16 g of a yellow, crystalline substance of raw loxoprofen was obtained.

The obtained raw loxoprofen was dissolved in a mixed solvent of 10 ml of ethyl acetate/10 ml of hexane, then recrystallized at 0° C. to obtain 4.92 g of a white, crystalline substance of loxoprofen. The purity by liquid chromatography was 99%. The NMR data and the retention time of liquid chromatography coincided completely with those of specimen.

According to the present invention, an industrial process can be provided which produces loxoprofen effectively using an inexpensive starting material. That is, adipic acid diester is used as a starting material, by which 2-substituted propionic acid can be produced more effectively than with conventional methods. Further, according to the present method, there is no need for apprehension about side reaction and the yield is higher.

What is claimed is:

1. A process for producing a compound as represented by the following general formula II (hereinafter referred to as "compound II"):

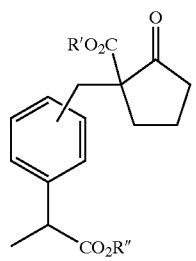

II wherein R' represents an alkyl group having 4 or less carbon atoms, R" represents a hydrogen atom or an alkyl group having 4 or less carbon atoms, and R' and R" can be either the same or different, which process comprises the steps of:

causing adipic acid diester to react with alkoxide as represented by the following general formula:

M(OR)$_n$ wherein R represents an alkyl group having 5 or less carbon atoms, M represents an alkali metal or alkaline earth metal, and n represents the number corresponding to the valence of M, and (OR)'s of n in number can be either the same or different, successively subjecting the product obtained above to coupling with halomethylstyrene to obtain a compound as represented by the following general formula I (hereinafter referred to as "compound I"):

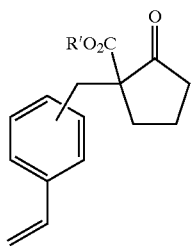

wherein R' represents an alkyl group having 4 or less carbon atoms, and causing said compound I to react with carbon monoxide and water or alcohol in the presence of a metal catalyst to obtain said compound II.

2. A process for producing 2-substituted propionic acid as represented by the following general formula III (hereinafter referred to as "compound III"):

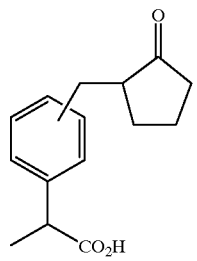

which process comprises the steps of (1-1) to (1-3):

step (1-1) to cause adipic acid diester to react with alkoxide as represented by the following general formula:

M(OR)$_n$ wherein R represents an alkyl group having 5 or less carbon atoms, M represents an alkali metal or alkaline earth metal, and n represents the number corresponding to the valence of M, and (OR)'s of n in number can be either the same or different, successively subjecting the product obtained above to coupling with halomethylstyrene to obtain the compound I as represented by the following general

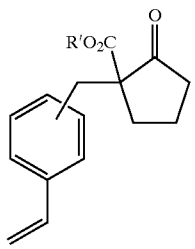

wherein R' represents an alkyl group having 4 or less carbon atoms, step (1-2) to cause said compound I to react with carbon monoxide and water or alcohol in the presence of a metal catalyst to obtain the compound II as represented by the following general formula II:

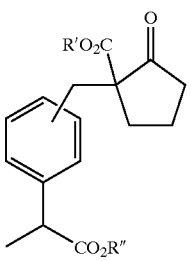

wherein R' represents an alkyl group having 4 or less carbon atoms, R" represents a hydrogen atom or an alkyl group having 4 or less carbon atoms, and R' and R" can be either the same or different, step (1-3) to subject said compound II to decarboxylation and hydrolysis to obtain said compound III.

3. A process as claimed in claim 1, wherein the halomethylstyrene is chloromethylstyrene.

4. A process for producing a compound II as represented by the following general formula II:

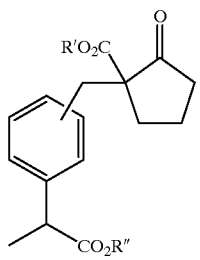

wherein R' represents an alkyl group having 4 or less carbon atoms, R" represents hydrogen atom or an alkyl group having 4 or less carbon atoms, and R' and R" can be either the same or different, which process comprises the steps of:

causing adipic acid diester to react with alkoxide as represented by the following general formula:

M(OR)$_n$ wherein R represents an alkyl group having 5 or less carbon atoms, M represents alkali metal or alkaline earth metal, and n represents the number corresponding to the valence of M and (OR)'s of n in number can be either the same or different, successively subjecting the product obtained above to coupling with a compound as represented by the following general formula IV (hereinafter referred to as "compound IV") to obtain said compound II,

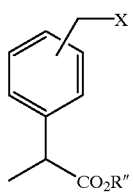

wherein X represents halogen atom, and R" represents hydrogen atom or an alkyl group having 4 or less carbon atoms.

5. A process for producing 2-substituted propionic acid as represented by the following formula III (compound III):

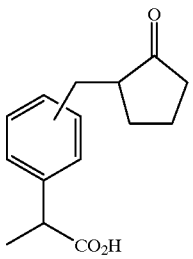

III which process comprises the steps of (2-1) and (2-2):
step (2-1) to cause adipic acid diester to react with alkoxide as represented by the following general formula:

M(OR)$_n$ wherein R represents an alkyl group having 5 or less carbon atoms, M represents alkali metal or alkaline earth metal, and n represents the number corresponding to the valence of M and (OR)'s of n in number can be either the same or different,
successively subjecting the product obtained above to coupling with a compound IV as represented by the following general formula IV to obtain the compound II as represented by the general formula II:

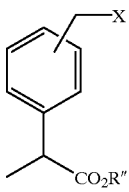

IV wherein X represents halogen atom, and R" represents hydrogen atom or an alkyl group having 4 or less carbon atoms, and

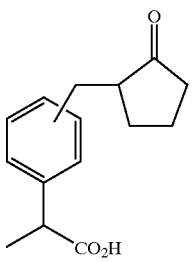

III wherein R' represents an alkyl group having 4 or less carbon atoms, R" represents hydrogen atom or an alkyl group having 4 or less carbon atoms, R' and R" can be either the same or different, and
step (2-2) to subject said compound II to decarboxylation and hydrolysis to obtain said compound III.

6. A process as claimed in claim 4, wherein the halogen atom X in said general formula IV is chlorine or bromine.

7. A process as claimed in claim 4, wherein R" in said general formula IV is a hydrogen atom, or a methyl or ethyl group.

8. A process as claimed in claim 1, wherein the effective amount of alkoxide M(OR)$_n$ is 0.7 to 1 equivalent relative to 1 mole of adipic acid diester in said reaction.

9. A process as claimed in claim 1, wherein the adipic acid diester is dimethyl adipate or diethyl adipate.

10. A process as claimed in claim 1, wherein the alkoxide M(OR)$_n$ is sodium methoxide or sodium ethoxide.

11. A process as claimed in claim 2, wherein the halomethylstyrene is chloromethylstyrene.

12. A process as claimed in claim 5, wherein the halogen atom X in said general formula IV is chlorine or bromine.

13. A process as claimed in claim 5, wherein R" in said general formula IV is a hydrogen atom, or a methyl or ethyl group.

14. A process as claimed in claim 6, wherein R" in said general formula IV is a hydrogen atom, or a methyl or ethyl group.

15. A process as claimed in claim 2, wherein the effective amount of alkoxide M(OR)$_n$ is 0.7 to 1 equivalent relative to 1 mole of adipic acid diester in said reaction.

16. A process as claimed in claim 3, wherein the effective amount of alkoxide M(OR)$_n$ is 0.7 to 1 equivalent relative to 1 mole of adipic acid diester in said reaction.

17. A process as claimed in claim 4, wherein the effective amount of alkoxide M(OR)$_n$ is 0.7 to 1 equivalent relative to 1 mole of adipic acid diester in said reaction.

18. A process as claimed in claim 5, wherein the effective amount of alkoxide M(OR)$_n$ is 0.7 to 1 equivalent relative to 1 mole of adipic acid diester in said reaction.

19. A process as claimed in claim 6, wherein the effective amount of alkoxide M(OR)$_n$ is 0.7 to 1 equivalent relative to 1 mole of adipic acid diester in said reaction.

20. A process as claimed in claim 7, wherein the effective amount of alkoxide M(OR)$_n$ is 0.7 to 1 equivalent relative to 1 mole of adipic acid diester in said reaction.

21. A process as claimed in claim 2, wherein the adipic acid diester is dimethyl adipate or diethyl adipate.

22. A process as claimed in claim 3, wherein the adipic acid diester is dimethyl adipate or diethyl adipate.

23. A process as claimed in claim 4, wherein the adipic acid diester is dimethyl adipate or diethyl adipate.

24. A process as claimed in claim 5, wherein the adipic acid diester is dimethyl adipate or diethyl adipate.

25. A process as claimed in claim 6, wherein the adipic acid diester is dimethyl adipate or diethyl adipate.

26. A process as claimed in claim 7, wherein the adipic acid diester is dimethyl adipate or diethyl adipate.

27. A process as claimed in claim 8, wherein the adipic acid diester is dimethyl adipate or diethyl adipate.

28. A process as claimed in claim 2, wherein the alkoxide M(OR)$_n$ is sodium methoxide or sodium ethoxide.

29. A process as claimed in claim 3, wherein the alkoxide M(OR)$_n$ is sodium methoxide or sodium ethoxide.

30. A process as claimed in claim 4, wherein the alkoxide M(OR)$_n$ is sodium methoxide or sodium ethoxide.

31. A process as claimed in claim 5, wherein the alkoxide M(OR)$_n$ is sodium methoxide or sodium ethoxide.

32. A process as claimed in claim 6, wherein the alkoxide M(OR)$_n$ is sodium methoxide or sodium ethoxide.

33. A process as claimed in claim 7, wherein the alkoxide M(OR)$_n$ is sodium methoxide or sodium ethoxide.

34. A process as claimed in claim 8, wherein the alkoxide M(OR)$_n$ is sodium methoxide or sodium ethoxide.

35. A process as claimed in claim 9, wherein the alkoxide M(OR)$_n$ is sodium methoxide or sodium ethoxide.

36. A process for producing a compound represented by the following formula II:

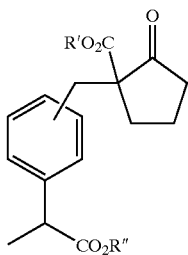

wherein R' represents an alkyl group having 4 or less carbon atoms, R" represents a hydrogen atom or an alkyl group having 4 or less carbon atoms, and R' and R" can be either the same or different, which process comprises:

obtaining a product by causing adipic acid diester to react with an alkoxide represented by the following formula:

M(OR)$_n$ wherein R represents an alkyl group having 5 or less carbon atoms, M represents an alkali metal or an alkaline earth metal, and n represents the number corresponding to the valence of M, and (OR)'s of n in number can be either the same or different, and successively subjecting the said product to coupling to produce said compound of formula II.

37. A process for producing a compound represented by the following formula III:

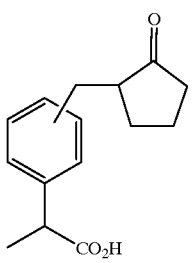

which process comprises:

obtaining a product by causing adipic acid diester to react with an alkoxide represented by the following formula:

M(OR)$_n$ wherein R represents an alkyl group having 5 or less carbon atoms, M represents an alkali metal or an alkaline earth metal, and n represents the number corresponding to the valence of M, and (OR)'s of n in number can be either the same or different, and successively subjecting the said product to coupling to obtain a compound represented by the following formula II:

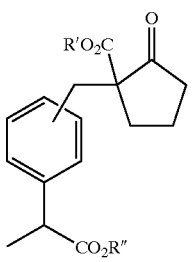

wherein R' represents an alkyl group having 4 or less carbon atoms, R" represents a hydrogen atom or an alkyl group having 4 or less carbon atoms, and R' and R" can be either the same or different, and subjecting said compound represented by formula II to decarboxylation and hydrolysis to obtain a 2-substituted propionic acid as represented by said formula III.

38. A process as claimed in claim 1, wherein in causing said compound I to react with carbon monoxide and water or alcohol in the presence of a metal catalyst to obtain said compound II a solvent is used in the amount of 10 times or less, by volume, based on the volume of compound I.

39. A process as claimed in claim 1, wherein in causing said compound I to react with carbon monoxide and water or alcohol in the presence of a metal catalyst to obtain said compound II a solvent is used in the amount of 0.5 to 3 times, by volume, based on the volume of compound I.

* * * * *